United States Patent [19]

Carmen et al.

[11] Patent Number: 4,855,063

[45] Date of Patent: * Aug. 8, 1989

[54] RED BLOOD CELL FILTERING SYSTEM

[75] Inventors: Raleigh A. Carmen, Concord; Chiyong Chong, San Francisco; Barry S. Leng, Pleasant Hill, all of Calif.

[73] Assignee: Miles Laboratories, Inc., Elkhart, Ind.

[ * ] Notice: The portion of the term of this patent subsequent to Mar. 7, 2006 has been disclaimed.

[21] Appl. No.: 854,287

[22] Filed: Apr. 21, 1986

[51] Int. Cl.$^4$ .................. B01D 21/26; B01D 29/08; B01D 36/00

[52] U.S. Cl. .................. 210/749; 210/787; 210/806; 210/807; 422/41; 422/44

[58] Field of Search .............. 210/787, 806, 807, 749; 422/41, 44; 494/37

[56] References Cited

U.S. PATENT DOCUMENTS

| 4,155,854 | 5/1979 | Marx | 210/435 |
|---|---|---|---|
| 4,596,657 | 6/1986 | Wisdom | 210/206 |
| 4,767,541 | 8/1988 | Wisdom | 210/749 |

OTHER PUBLICATIONS

Kleesiek, K. et al., "Elastase from Granulocytes . . . ", Abstract, p. 01, 18th Cong. Int. Soc. Blood Transf., Munich, 7/22–27/84.
Jochum, M. et al., "Release of Granulocytic . . . ", Abstract, p. 2, 18th Cong. Int. Soc. Blood Transf. Munich, 7/22–27/84.
Kigugawa, K. et al., "Filter Columns . . . ", Vox Sang, vol. 34, pp. 281–290, 1975.
Diepenhorst, P. et al., "Removal of Leukocytes . . . ", Vox Sang, vol. 23, pp. 308–320, 1972.
Diepenhorst, P. et al., "Removal of Leukocytes from Whole Blood . . . ", Vox Sang, vol. 29, pp. 15–22, 1975.
Dern, R. J. et al, "Studies on the Preservation of Human Blood . . . ", J. Lab. Clin. Med., vol. 69, No. 6, pp. 968–978, 1967.
Strehler, Bernard, "Adenosine-5'-Triphosphate . . . ", in Bergmeyer, Editor, 4th Printing, 1974, Acad. Press, N.Y., pp. 2112–2121.

Primary Examiner—W. Gary Jones
Attorney, Agent, or Firm—James A. Giblin

[57] ABSTRACT

Closed filtering system for relatively fast and efficient removal of white blood cells from a red blood cell mixture. System comprises at least two blood bags in closed communication with each other via an intermediate filter assembly comprising a housing containing continuous filtering fiber. A preferred housing is tapered and the fiber preferably has a generally Y-shaped cross sectional area and it is adapted to permit substantial removal of white blood cells from a red blood cell mixture with minimal red blood cell hemolysis when the mixture is diluted with perservative solution and passed from one bag to the other at a relatively high flow rate. Filtration is completed within 24 hours, preferably within 6 hours, of whole blood donation.

6 Claims, 3 Drawing Sheets

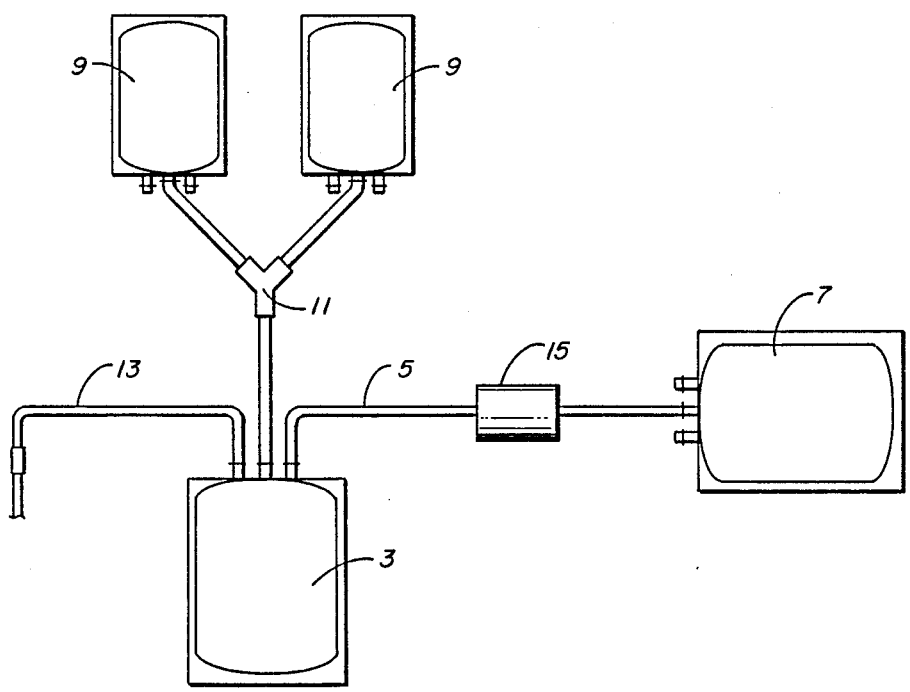
FIG._1
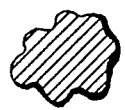
FIG._2A
(PRIOR ART)
FIG._2B

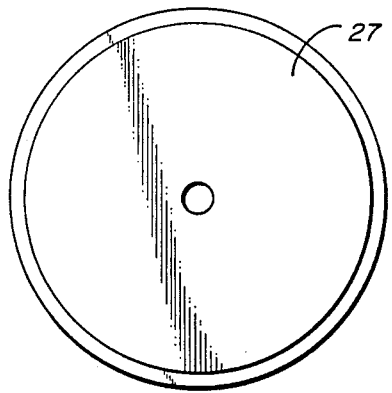
(PRIOR ART)
FIG._4A
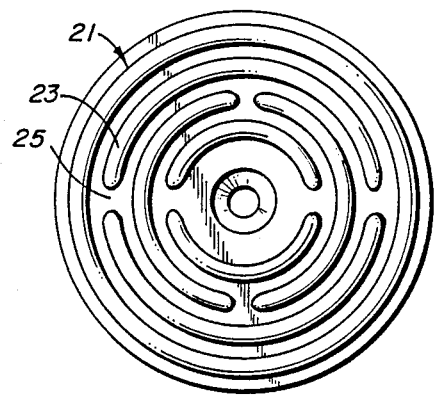
FIG._4B
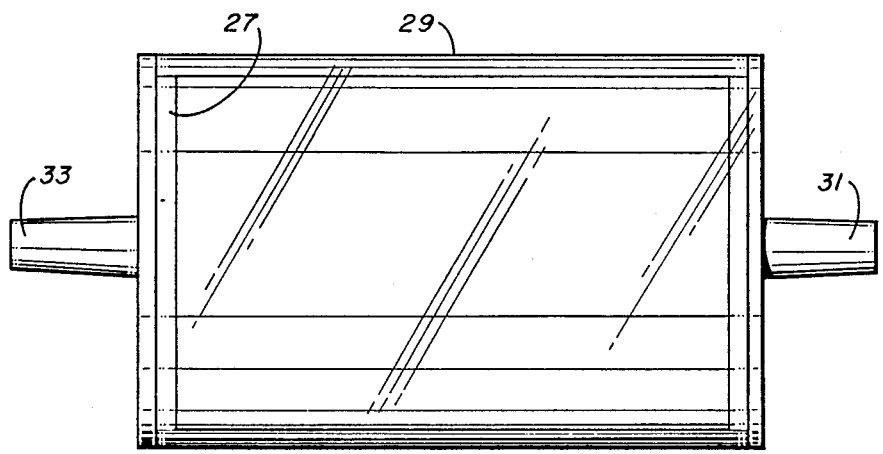
FIG._3A (PRIOR ART)
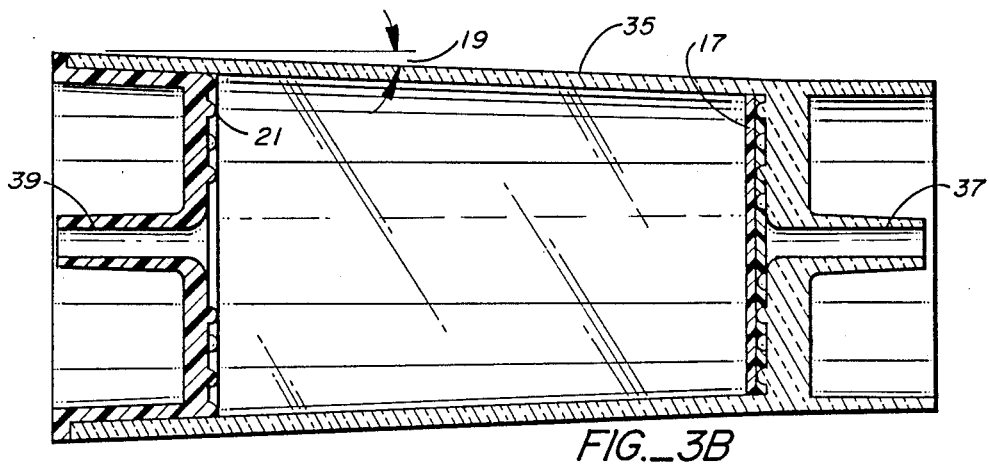
FIG._3B

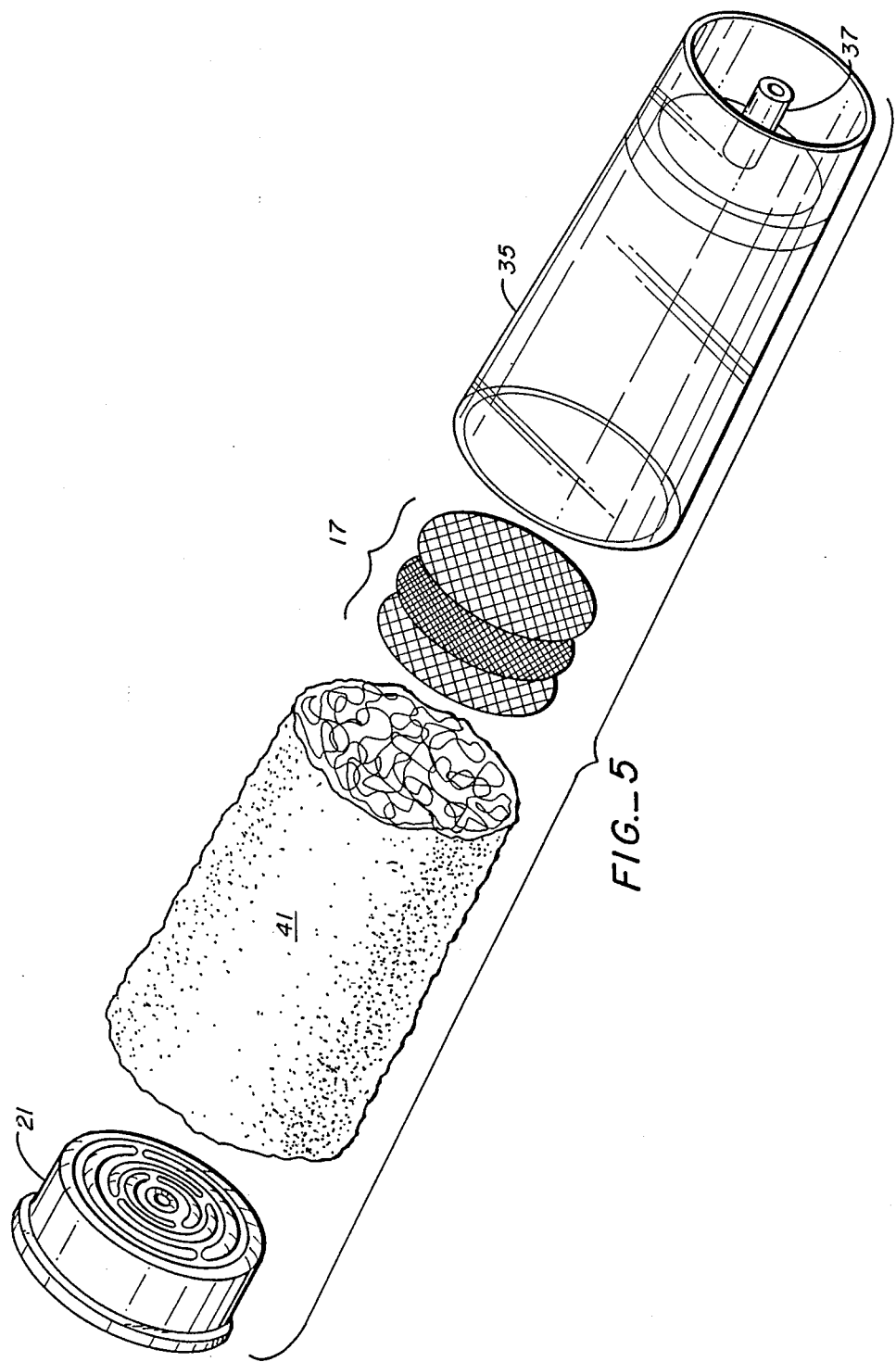

RED BLOOD CELL FILTERING SYSTEM

BACKGROUND OF THE INVENTION

1. Field

This disclosure is concerned generally with blood filtering systems and specifically with a system for the removal of white blood cells from red blood cells.

2. Prior Art

The desirability of removing white blood cells (WBC) from a mixture of WBCs and red blood cells (RBC) is well known, especially for patients who receive frequent blood transfusions. See, for example abstracts by K. Kleesiek et al (P-9-01) and M. Jochum et al (p-9-02) from Abstracts of the 18th Congress of the International Society of Blood Transfusion, Munich, July 22-27, 1984. See also the article by H. Harke et al, Anaesthesist (1982) 31:165-171.

In the past, WBCs and platelets associated with febrile reactions have been removed via the reconstitution of frozen blood (which is costly) or by multiple washings with saline of the RBC/WBC mixture (which is time consuming, is less predictable, and results in RBC loss).

Kikugawa et al in Vox Sang., Vol. 34, 281-290 (1975) describe commercial cotton wool filters for filtering blood to remove the above HLA antigen. These filters are, however, expensive and cumbersome to use.

Diepenhorst et al in Vox Sang., Vol. 23, 308-320 (1972) and Vol. 29, 15-22 (1975) disclose cotton wool filtration of blood under pressure. This method, while efficient, requires a special apparatus that is expensive.

All of the above techniques require that the treated blood be infused within 24 hours of treatment in order to avoid the potential risk of infection. Prolonged shelf life of blood so treated is not possible.

Some of the above shortcomings have been addressed in patent application Ser. No. 06/385,167 now U.S. Pat. No. 4,596,657, filed in the name of L. Wisdom on June 4, 1982, entitled "Blood Bag System with Integral Filtering Means", the teachings of which are incorporated herein by reference thereto. The present disclosure represents an improvement over the system and methods disclosed in that application and details of the improved system and method of filtration are described below.

SUMMARY OF THE INVENTION

Our red blood cell filtering system comprises a closed multiple blood bag system comprising at least two flexible plastic bags in closed communication with each other via connecting plastic tubing. Intermediate the bags and continuous with the connecting plastic tubing is a white blood cell filter. The filter comprises a preferably slightly tapered housing containing continuous filtering fiber adapted to substantially remove WBCs from a mixture of WBCs and RBCs with minimal RBC hemolysis when the mixture is passed from one bag to the other through the filter at a relatively high flow rate. In preferred embodiments filtration is completed within 24 hours (very preferably within 6 hours) of whole blood donation and at a low temperature (e.g. less than 6° C). The continuous filtering fiber preferably is a cellulose acetate material and, in a preferred embodiment, has a generally Y-shaped cross sectional area and a packed bulk of less than about 0.6 grams per cc and a continuous fiber length of greater than 1000 meters. The preferred filter has a volume of less than about 50 cc and yet is capable of filtering a unit of blood (about 225 ml of packed RBCs subsequently diluted to about 325 ml total with a RBC additive or preservative solution) in less than 3 hours at room temperature. The preferred filter can remove over 80% of the WBCs in a WBC/RBC mixture at the above rate with a RBC hemolysis after five weeks storage of less than 0.30%. In a very preferred embodiment, one of the bags includes a RBC preservation solution which is used to prime the filter prior to the filtration step.

BRIEF DESCRIPTION OF THE FIGURES

FIG. 1 is a plan view of a multiple blood bag filtering system of the type disclosed herein.

FIGS. 2A and 2B compare the cross sectional areas of the fiber of patent application Ser. No. 06/385,167, now U.S. Pat. No. 4,596,657, cited above, with the continuous, preferred fiber of the present invention.

FIGS. 3A and 3B compare a cross sectional view of the filter housing of this disclosure (3B) with that of the housing of Ser. No. 06/385,167, now U.S. Pat. No. 4,596,657 (3A).

FIGS. 4A and 4B compare the filter retainers of the above described filters.

FIG. 5 illustrates an exploded view of the preferred filter of the invention.

SPECIFIC EMBODIMENTS

The inline RBC filtering system of this disclosure can be understood better by reference to the Figures.

FIG. 1 illustrates a whole blood collection bag (donor bag) 3 in continuous closed communication via plastic tubing 5 and filter 15 with an additive (preservative) solution bag 7 and one or more satellite bags 9 connected via a typical Y-connector 11. Also in communication with the donor bag is blood collection tubing 13 which includes at its distal end (not shown) a blood donor needle of the common type used in the art (not shown). The system of FIG. 1 may include various internal valves of the types well known in the art for containing or moving one or more components of blood through the closed filtering system. As used herein, the term "closed" refers to a blood collection system which allows the collection, storage, processing, separation filtration and preservation of donor whole blood or blood components without the need to enter the system (and risk contamination of the system). Such a closed system may be originally made as an internal one piece unit or, result from the connection of the individual (or partially connected) components of such a system using what are known as "sterile docking" devices of the type shown, for example, in U.S. Pat. No. 4,507,119.

The system of FIG. 1 is used as follows: Whole blood is collected via tubing 13 from a donor into donor or collection bag 3 which typically contains an anticoagulant solution. The whole blood is then centrifuged using normal procedures (e.g. 3000 rpm for 2 minutes) to separate the blood into denser packed red blood cells and less dense platelet rich plasma. By opening a conventional valve (not shown) between donor bag 3 and one of the satellite bags 9, the platelet-rich plasma may be expressed into one of the satellite bags by known means (e.g., by using a plasma expressor), leaving behind the packed red blood cells in donor bag 3. The packed RBCs include both WBCs and some platelets, both of which should be removed if possible before us or storage. This is accomplished by reconstituting the RBC mixture with an additive solution, preferably already in the closed system and available from additive solution bag 7, by merely expressing the solution from bag 7 through filter 15 (in the non-filtering direction) into donor bag 3 for mixture with and dilution of the RBC mixture. Additive (or preservative) solutions for RBCs are well known and described in numerous publications. Two such solutions are described in the Examples below. This pre-filtering flow of additive solution through the filter into the bag of (packed) RBCs allows reconstitution and provides a viscosity for the RBCs that is beneficial for filtration. In addition, the additive solution primes the filter for the important filtration step with the RBC/additive solution. This initial priming is important because it is a necessary step to prepare the filter for efficient white blood cell removal. In particular it allows the cellulose acetate material to absorb water and flushes the air void volume of the filter.

The above steps can all be accomplished by known means via external manipulation of the bags or internal valves, thus keeping the system "closed" to outside contaminants. After the RBC mixture has been reconstituted with the additive solution, the reconstituted mixture is passed in a forward filtering direction through filter 15 by gravity at which time most of the WBCs and remaining platelets are removed by the filter, allowing the filtered RBCs, already in an additive/preservation solution, to be stored in bag 7 which can be clamped and removed from the system for long term storage, preferably for up to 6 weeks. The platelet-rich plasma in one of the satellite bags 9 can be further processed (e.g. by centrifugation at higher speeds, etc.) to separate the mixture into yet further components (platelets and plasma components) by other known means.

FIG. 2B shows a cross section of the preferred present filter fiber of this disclosure having a generally Y-shaped cross sectional area and compares it with the earlier fiber of co-pending Ser. No. 06/385,167, now U.S. Pat. No. 4,596,657, FIG. 2A. It is important to note that the filtering fiber of this invention is "continuous", that is, an essentially single strand of fiber that may be up to 9000 meters long. This is unlike the chopped filter material of the prior art which is undesirable because potential loose short (3.2 cm) fibers of the prior art might pass through a fiber-retaining screen and into the final product.

FIGS. 3A and 3B compare the cross section of the filter housing of the filter of this disclosure (3B) with that of the earlier housing of Ser. No. 06/385,167, now U.S. Pat. No. 4,596,657, and illustrates how the housing of this disclosure is slightly tapered at one end to assist in the filtering process.

As can be seen in Prior Art housing 3A, the housing in cross section appears rectangular and is not tapered as in housing 35 of this invention, FIG. 3B. The taper of the housing 35 of FIG. 3B is defined by an angle of about 2 degrees, as illustrated at 19 of FIG. 3B. Such tapering assures the prevention of any channelling within the filter potentially resulting in unfiltered white blood cells in the final product.

Both FIGS. 3A and 3B have inlet and outlet ports 33, 31, 39 and 37 and members 27 and 21 adapted to assist in retaining the filter fiber (41 of FIG. 5). In the present filter, however, the fiber retaining member 21 has interrupted ridges 23 and channels 25. The ridges are used to support the fused screen and prevent blocking of the outlet port 37. Also, the ridges provide a continuous pathway for the leukocyte poor red cells to exit the filter.

The present filter also includes at the opposite (smaller) end within housing 35 a fused screen (see 17 in FIG. 3B and, in exploded form, 17 in FIG. 5). The screen is designed to retain fiber material and prevent fiber blockage of inlet and outlet ports and is preferably made by sonic energy fusion of polyester screens. Two each 1000 micrometer mesh size screens sandwich a 27 micrometer pore size screen to form a single unit.

The preferred fiber is a "continuous" cellulose acetate (obtained, for example, from Celanese Corp. and known as Celanese brand cellulose acetate "TOW" filter material). Other continuous fibers include polyester, cotton wool, and polypropylene.

The filter housing itself may be made from polycarbonate. Other details on the filter and bags (how made and connected) may be found in copending Ser. No. 06/385,167, now U.S. Pat. No. 4,596,657.

The filter of this disclosure compared in physical properties with that of Ser. No. 06/385,167, now U.S. Pat. No. 4,597,657, as follows:

TABLE I

|  | Earlier Disclosure | This Disclosure |
| --- | --- | --- |
| Fiber: | Cellulose Acetate (Staple) | Cellulose Acetate (Tow) |
| Fiber length: | ~3.2 cm | >1000 m |
| Shape (x.c.): | gen. circular | gen. Y shaped |
| Housing Vol.: | 55 cc | 48 cc |
| Fiber weight: | 35 g | 25 g |
| Density: | 0.636 g/cc | 0.521 g/cc |
| Flow time (unit)* (at room temperature): | 4.2 ± 0.8 h | 2.3 ± 0.4 h |
| 90 WBC removal (at room temperature): | 84 ± 9% | 87 ± 9% |

*one unit - about 250-300 ml of reconstituted RBCs.

DISCUSSION OF DIFFERENCES

As can be seen from the above Table, the filter of this disclosure uses about 30% by weight less fiber without compromising WBC removal. Quite surprisingly, this is done while significantly reducing the flow time. As can be seen, the flow time is reduced by almost one-half, a convenience to the user and a useful feature in cases where filtered RBCs are needed in a hurry.

Effects of WBC Titration on RBCs with Time:

In a preferred embodiment of the invention disclosed herein, the WBCs are removed via filtration from the RBC/WBC mixture as soon as possible (i.e. within 24 hours) after whole blood collection so that the WBCs have as little contact as possible with the RBCs during storage, which can be up to 6 weeks. The effects of WBC removal using the filtration system disclosed herein were surprising when both hemolysis and 2,3-DPG levels of the stored RBCs were measured over varying periods of time both with and without using the filtering system of this invention.

Hemolysis Studies:

The amounts of hemolysis at 5, 6 and 7 week storage periods were compared for filtered and non-filtered RBCs using two different RBC storage solutions designated "AS-3" and "AS-5" additive systems. In cases where the filtering system of this disclosure was used, filtration was done within about 6 hours of blood donation and gross separation. The AS-3 and AS-5 additive systems (for up to 42 day RBC storage) used in the examples had the following ingredients per 100 ml additive solution:

TABLE II

| AS-3 Additive Solution (per 100 ml) | |
| --- | --- |
| Dextrose - $H_2O$ | 1100 mg |
| Sodium Chloride | 410 mg |
| Citric Acid - $H_2O$ | 42 mg |
| Sodium Citrate - $2H_2O$ | 588 mg |
| Monobasic Sodium Phosphate - $H_2O$ | 276 mg |
| Adenine | 30 mg |
| Water q.s. | |

TABLE III

| AS-5 Additive Solution (per 100 ml) | |
| --- | --- |
| Trisodium-L-Ascorbate-2-Phosphate | 230 mg |
| Sodium Chloride | 450 mg |
| Adenine | 30 mg |
| Sodium Phosphate (anhydrous) | 400 mg |
| Mannitol | 750 mg |
| Water q.s. | |

Using the above storage solutions, RBC hemolysis was measured by direct spectrophotometry as described by Blakney and Dinwoodie, Clin. Biochem. 1975; 8:96–102 and the results over varying periods are shown in Tables IV and V, below.

TABLE IV

Hemolysis for AS-3 Additive Systems

| Condition | Week 5 | Week 6 | Week 7 |
| --- | --- | --- | --- |
| AS-3 Filtered @ 5° C. n = 4 | 0.28 ± 0.20 | 0.36 ± 0.25 | 0.37 ± 0.25 |
| AS-3 Filtered @ RT n = 4 | 0.17 ± 0.04 | 0.22 ± 0.06 | 0.28 ± 0.08 |
| x ± SD n ± 8 | 0.23 ± 0.15 | 0.29 ± 0.18 | 0.33 ± 0.18 |
| AS-3 Unfiltered n = 3 | 0.21 ± 0.06 | 0.48 ± 0.10 | 0.79 ± 0.06 |
| AS-3 Unfiltered n = 3 | 0.30 ± 0.14 | 0.80 ± 0.33 | 0.93 ± 0.55 |
| AS-3 Unfiltered n = 4 | 0.61 ± 0.64 | — | 1.02 ± 1.04 |
| AS-3 Unfiltered n = 4 | — | 0.66 ± 0.22 | — |
| x ± SD n = 10 | 0.40 ± 0.42 | 0.52 ± 0.27 | 0.93 ± 0.66 |

TABLE V

Hemolysis for AS-5 Additive Systems

| Condition | Week 5 | Week 6 | Week 7 |
| --- | --- | --- | --- |
| AS-5 Filtered @ 22° C. n = 4 | 0.16 ± 0.02 | 0.24 ± 0.05 | 0.38 ± 0.09 |
| AS-5 Filtered @ 5° C. n = 4 | 0.21 ± 0.15 | 0.27 ± 0.18 | 0.44 ± 0.35 |
| x ± SD n = 8 | 0.18 ± 0.10 | 0.25 ± 0.13 | 0.41 ± 0.24 |
| AS-5 Unfiltered n = 4 | 0.46 ± 0.15 | 0.64 ± 0.27 | — |
| AS-5 Unfiltered n = 3 | 0.73 ± 0.11 | 1.01 ± 0.18 | — |
| AS-5 Unfiltered n = 4 | 0.45 ± 0.19 | 0.65 ± 0.33 | — |
| x ± SD n = 11 | 0.53 ± 0.19 | 0.74 ± 0.30 | — |
| Statistics | $P = <0.01$ | $P = <0.01$ | |

2,3-DPG Studies:

Using the filtering system of this disclosure and the AS-5 additive solution, 2,3-DPG levels (a measure of RBC oxygen affinity or RBC function) were determined and compared with non-filtered RBCs. Results are shown in Table VI.

TABLE VI 2,3-DPG Date for AS-5 % of Initial

| Condition | Week 3 | Week 5 | Week 7 |
| --- | --- | --- | --- |
| AS-5 Filtered @ RT n = 4 | 194% | 160 | 102 |
| AS-5 Filtered @ 5° C. n = 4 | 172% | 128 | 104 |
| AS-5 Unfiltered n = 4 | 158% | 108 | — |
| AS-5 Unfiltered n = 3 | 171% | 110 | — |

In use, whole blood should be filtered with the above filtering system as soon as possible after collection from a donor. As a practical matter, this should be within 24 hours of whole blood collection but, very preferably, the filtration is completed within about 6 hours of whole blood collection and the filtration should be at a low temperature (at least as low as 25° C., or in the range of about 4 to 25° C.

ATP Levels in Filtered (F) vs. Unfiltered (C) Blood:

ATP levels of filtered and unfiltered blood were compared. Each unit of blood (six in all) had a portion drawn and stored as the control (C=unfiltered) sample before filtration occurred. The results are summarized below:

TABLE VII

ATP ($\mu$M/gHb)

| | WEEK 5 | | WEEK 6 | |
| --- | --- | --- | --- | --- |
| DONOR | F | C | F | C |
| 273 | 4.0 | 3.7 | 3.5 | 2.6 |
| 274 | 5.1 | 4.7 | 5.0 | 4.3 |
| 275 | 4.3 | 3.8 | 3.7 | 3.2 |
| 276 | 3.5 | 3.7 | 3.2 | 3.0 |
| 277 | 4.1 | 3.4 | 3.3 | 2.4 |
| 278 | 2.6 | 2.0 | 2.2 | 1.6 |
| x ± SD | 3.9 ± 0.8 | 3.6 ± 0.9 | 3.5 ± 0.9 | 2.9 ± 0.9 |
| | $p < 0.03$ | | $p < 0.01$ | |

ATP Levels in filtered samples were significantly higher (n=6) compared to corresponding unfiltered control samples at both Week 5 and Week 6. In general, ATP levels tend to correlate with in vivo recovery. (Dern et al, *J. Lab. Clin. Med.*, Vol. 69, 968–978, 1967).

Usual comparisons to initial samples cannot be made since initial samples were not measured. ATP levels were determined by the method of enzymatic analysis, H-U Bergmeyer, ed. 2nd printing, rev. 1965. Acad. Press, New York, pp. 559–572.

Given the above disclosure, it is thought numerous variations will occur to those skilled in the art. Accordingly, it is intended that the above example should be construed as illustrative only and that the inventions disclosed herein be limited only by the following claims.

We claim:

1. A method of filtering at least about 80% of the white blood cells from a mixture of red blood cells and white blood cells from a unit of reconstituted red blood cells in less than about 24 hours and with minimal long term hemolysis of the red blood cells, the method comprising the steps of (a) providing a closed multiple blood bag system comprising two blood bags in closed communication with each other via connecting plastic tubing and, including continuous with the plastic tubing a tapered white blood cell filter housing containing a continuous filtering fiber having a generally Y-shaped cross sectional area and a bulk density of less than about 0.6 gram per cc, one of the blood bags being a first bag adapted to include the mixture of red and white blood cells and the other bag being the second bag and including a red blood cell storage solution;

(b) introducing the storage solution into the first bag by passing the solution through the filter to prime the filter and removing air from the filter and then mixing the solution with the red and white blood cells; and (c) passing the mixture of step (b) through the filter and into the second bag under conditions sufficient to remove at least about 80% of the white blood cells from the mixture in less than about 24 hours, thereby providing a red blood cell preparation substantially free of white blood cells and suitable for long term storage without substantial amounts of white blood cell contaminants and with minimal red blood cell hemolysis.

2. The method of claim 1 wherein the filtration of step (c) is completed within less than about 6 hours.

3. The method of claim 1 wherein the taper of the filter housing is toward the second bag and is defined by an angle of about 2 degrees and adapted to prevent the channelling of the mixture passing through the filter into the second bag.

4. The method of claim 1 wherein the continuous filtering fiber has a fiber length of greater than about 1000 meters.

5. The method of claim 1 wherein the filter housing has a volume of less than about 50 cc.

6. The method of claim 1 wherein the filtering of step (c) is completed in less than about 3 hours and at room temperature.

* * * * *